(12) United States Patent
Vogt

(10) Patent No.: US 9,744,316 B2
(45) Date of Patent: Aug. 29, 2017

(54) MEDICAL SPRAYING DEVICE WITH NOZZLE, AND METHOD FOR PRODUCING A SPRAY CONE

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

(*) Notice: Subject to any disclaimer, the term of this patent is extended or adjusted under 35 U.S.C. 154(b) by 460 days.

(21) Appl. No.: 14/297,665

(22) Filed: Jun. 6, 2014

(65) Prior Publication Data

US 2014/0364816 A1 Dec. 11, 2014

(30) Foreign Application Priority Data

Jun. 6, 2013 (DE) .......................... 10 2013 210 539

(51) Int. Cl.
*A61M 11/00* (2006.01)
*A61M 3/02* (2006.01)
(Continued)

(52) U.S. Cl.
CPC ........ *A61M 11/006* (2014.02); *A61M 3/0233* (2013.01); *A61M 3/0254* (2013.01);
(Continued)

(58) Field of Classification Search
CPC A61M 11/006; A61M 3/0233; A61M 3/0254; A61M 3/0279; B05B 1/265; B05B 7/2421
See application file for complete search history.

(56) References Cited

U.S. PATENT DOCUMENTS 2,323,464 A 7/1943 Glessner
2,631,891 A * 3/1953 Kochner ............... B05B 7/2416
141/19
(Continued)

FOREIGN PATENT DOCUMENTS

CN 1568202 A 1/2005
CN 102218181 A 10/2011
(Continued)

OTHER PUBLICATIONS

Australian Office Action for corresponding Australian Application No. 2014202803 dated Oct. 21, 2014.
(Continued)

*Primary Examiner* — Leslie Deak
*Assistant Examiner* — Kai Weng
(74) *Attorney, Agent, or Firm* — Norris McLaughlin & Marcus, P.A.

(57) ABSTRACT

A medical spraying device and method, for irrigating a wound, having a liquid reservoir for a medical irrigation liquid or a connection for such a liquid reservoir and an arrangement for applying pressure to the medical irrigation liquid, such that the irrigation liquid is pushable through a nozzle by the pressure acting on the irrigation liquid in order to produce a spray cone. The nozzle has a plurality of openings, which are arranged at an angle to one another in such a way that the irrigation liquid jets exiting from the openings, at a such flow rate and angle, meet in an atomization space and/or a discharge opening of the nozzle; thus, a spray cone is produced from the atomized irrigation liquid.

22 Claims, 2 Drawing Sheets

Figure 1:
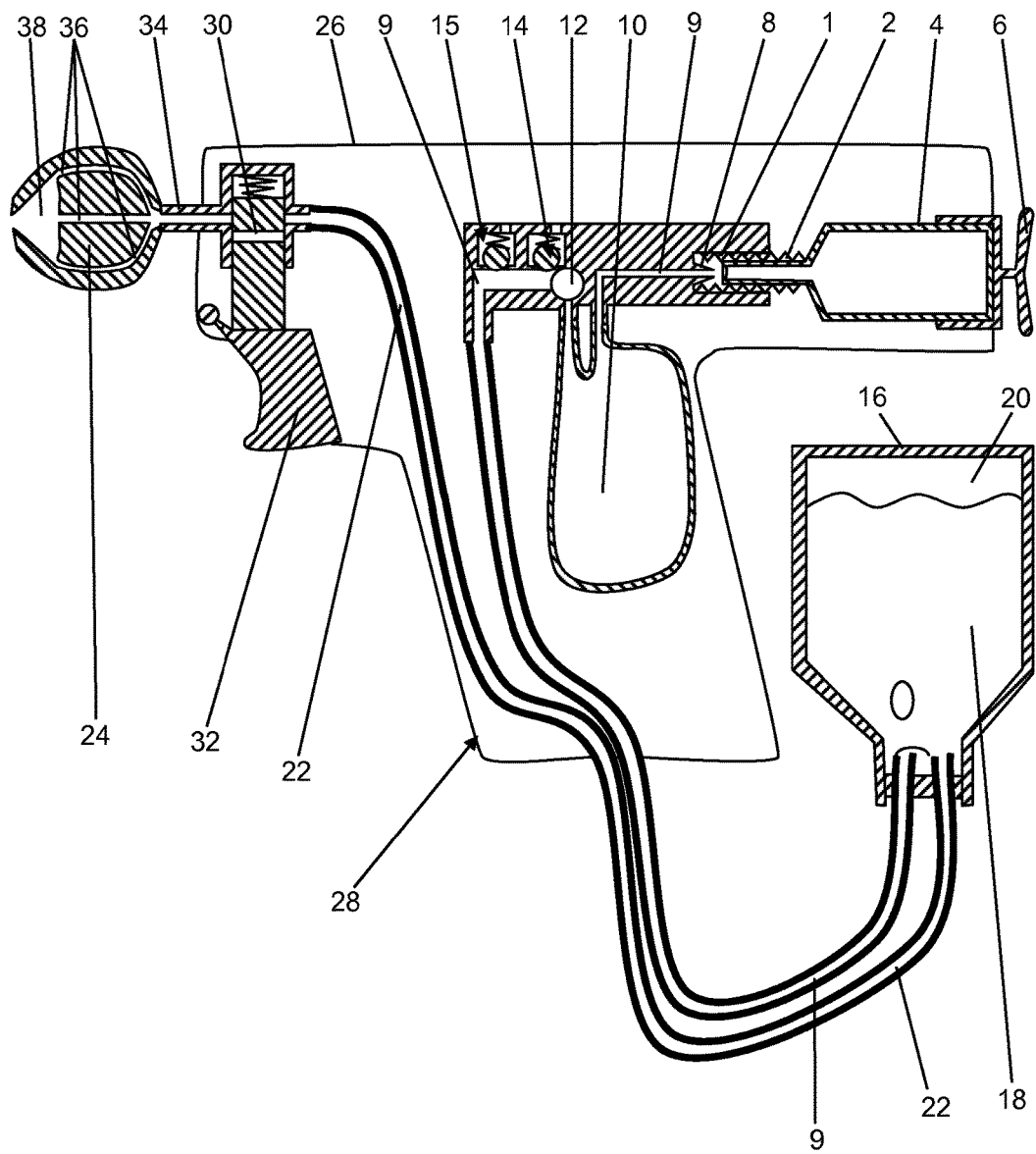

(51) Int. Cl.
  *B05B 1/26* (2006.01)
  *B05B 7/24* (2006.01)
(52) U.S. Cl.
  CPC .......... *A61M 3/0279* (2013.01); *B05B 1/265* (2013.01); *B05B 7/2421* (2013.01)

(56) References Cited

U.S. PATENT DOCUMENTS

| | | | | |
|---|---|---|---|---|
| 2,717,804 | A | * | 9/1955 | White, Jr. .............. B05B 7/2421 239/112 |
| 2,785,926 | A | | 3/1957 | Lataste |
| 4,157,093 | A | * | 6/1979 | Brodsky ............. A61M 3/0233 604/147 |
| 4,278,078 | A | | 7/1981 | Smith |
| 4,583,531 | A | | 4/1986 | Mattchen |
| 4,681,262 | A | * | 7/1987 | Sprute .................. B05B 7/2416 239/306 |
| 5,542,918 | A | | 8/1996 | Atkinson |
| 5,830,197 | A | | 11/1998 | Rucinski |
| 2001/0037095 | A1 | | 11/2001 | Rucinski |
| 2003/0108487 | A1 | * | 6/2003 | Bara ..................... A45D 34/04 424/47 |
| 2004/0180442 | A1 | | 9/2004 | Lin et al. |
| 2007/0040046 | A1 | | 2/2007 | Dorendorf et al. |
| 2008/0311010 | A1 | | 12/2008 | Boe |
| 2009/0194099 | A1 | | 8/2009 | Kladders |
| 2011/0041844 | A1 | | 2/2011 | Dunne |
| 2011/0253805 | A1 | | 10/2011 | Lee |
| 2013/0001331 | A1 | | 1/2013 | Palle |

FOREIGN PATENT DOCUMENTS

| | | |
|---|---|---|
| CN | 103006323 A | 4/2013 |
| DE | 10004534 A1 | 8/2001 |
| DE | 10300983 A1 | 7/2004 |
| DE | 69832640 T2 | 6/2006 |
| DE | 102011018708 A1 | 10/2012 |

OTHER PUBLICATIONS

German Office Action for corresponding German Application No. 10 2013 210 539.8 dated Feb. 18, 2014.

Sherman, et al., "The Role of Lavage in Preventing Hemodynamic and Blood-Gas Changes During Cemented Arthroplasty," The Journal of Bone and Joint Surgery, Incorporated; Apr. 1983, vol. 65-A, No. 4, pp. 500-506, Toronto, Ontario, Canada.

Breusch, et al., "Lavage Technique in Total Hip Arthroplasty, Jet Lavage Produces Better Cement Penetration Than Syringe-Lavage in the Proximal Femur," The Journal of Arthroplasty; 2000, pp. 921-927, vol. 15, No. 7; Churchill Livingstone; Heidelberg, Germany.

Christie, et al., "Medullary Lavage Reduces Embolic Phenomena and Cardiopulmonary Changes During Cemented Hemiarthroplasty," British Editorial Society of Bone and Joint Surgery; May 1995, vol. 77-B, No. 3, pp. 456-459, United Kingdom.

Byrick, et al., "High-volume, High-Pressure Pulsatile Lavage During Cemented Arthroplasty," The Journal of Bone and Joint Surgery, Incorporated; Oct. 1989, vol. 71-A, No. 9, pp. 1331-1336, Toronto, Ontario, Canada.

Chinese Office Action for corresponding Chinese Application No. 201410251023.X dated Dec. 13, 2016.

* cited by examiner

MEDICAL SPRAYING DEVICE WITH NOZZLE, AND METHOD FOR PRODUCING A SPRAY CONE

The invention relates to a medical spraying device for irrigating a wound, in particular a lavage system, and to the use of such a spraying device.

The invention furthermore also relates to a method for producing a spray cone with a medical spraying device.

The invention thus relates to a medical spraying device, driven by compressed gas, for trauma surgery and orthopaedics. The spraying device can be constructed substantially of plastics and is preferably intended for one-time use.

Medical spraying devices are often referred to in the medical field as lavage systems. Lavage systems are used widely in surgery during operations (OPs) in order to clean tissue areas. Here, physiological saline solution and Ringer's solution are often used as irrigation liquids. With the lavage systems, spray cones or spray jets are produced with the irrigation liquids and impinge on the tissue areas to be cleaned and exert a mechanical cleaning effect on these tissue areas. In particular in the case of the implantation of joint endoprostheses and in the case of septic revisions, lavage systems are of significant importance (R. M. Sherman et al.: The role of lavage in preventing hemodynamic and blood-gas changes during cemented arthroplasty. J. Bone Joint. Surg. 1983; 65-A: 500-506.; S. J. Breusch et al.: Lavage technique in THA: Jet-lavage Produces Better Cement Penetration Than Syringe-Lavage in the Proximal Femur. J. Arthroplasty. 200; 15(7): 921-927.; R. J. Byrick et al.: High-volume, high pressure pulsatile lavage during cemented arthroplasty. J. Bone Joint Surg. 1989; 81-A: 1331-1336.; J. Christie et al.: Medullary lavage reduces embolic phenomena and cardiopulmonary changes during cemented hemiarthorplasty. J. Bone Joint Surg. 1995; 77-B: 456-459.). Pulsed lavage systems are known from U.S. Pat. No. 4,583,531 A, U.S. Pat. No. 4,278,078 A and U.S. Pat. No. 5,542,918 A. DE 698 32 640 T2 discloses a device for wound irrigation in which liquid jets meet in front of a nozzle.

The lavage systems currently on the market are driven by electric motors (for example InterPulse® Jet lavage by Stryker GmbH & Co. KG) or by compressed air (for example PALAVAGE® by Heraeus Medical GmbH). In the case of electrically driven lavage systems, however, a large battery block or accumulator block always also has to be carried and naturally has only a limited charge capacity. Battery and accumulator blocks are criticised in terms of the environmental friendliness thereof. Lavage systems driven by compressed air have the advantage that compressed air is often available in the operating theatre in an unlimited amount, and irrigation liquid can thus be sprayed for as long as desired without limiting the energy feed.

In the case of the systems driven with compressed air or another compressed gas, a compressed gas motor is usually used for drive purposes. Most compressed gas motors for lavage systems are multi-disc compressed gas motors. The compressed gas motor generates a rotational movement, which is then converted into an oscillating, linear movement. The oscillating, linear movement is used to pulse small volumes of the irrigation medium. Here, at least one membrane is usually arranged between the drive and the inflow of the irrigation liquid so as to be able to transmit the pulses to the irrigation liquid. Puffs of spray are thus created with high pulse rates from 2,000 to 3,000 pulses per minute. This means that the compressed gas motor has to be manufactured very precisely in order to tolerate correspondingly high rotational speeds. Furthermore, a correspondingly stable mounting has to be provided. For these reasons, the compressed gas motor is the most costly component in conventional lavage systems driven by compressed air. The compressed gas motor is therefore generally arranged in a handle made of metal or other materials stable in the long term, such that this component can be used a number of times following appropriate preparation and sterilisation.

A disadvantage here is that the construction of many known lavage systems is relatively complicated and thus costly. Due to the construction with a motor there is always a risk of malfunction of the motor and therefore a malfunction of the lavage system. In the case of a multiple use, the lavage systems have to be disinfected and prepared. Since errors may occur during the disinfection, a contamination of the wounds of the patient and therefore a complicated infection cannot be ruled out. The noise generated by the motor in OP operation is also bothersome and annoying for the medical personnel.

One object of the invention is therefore to overcome the disadvantages of the prior art. In particular, a medical spraying device is to be provided that can be manufactured as inexpensively as possible and that produces a spray cone suitable for debriding wounds.

A further object of the invention is to develop a medical spraying device which can be manufactured easily, is constructed as simply as possible and can be intended for one-time use. The construction of the spraying device is to be simplified to the maximum and is to consist of minimal parts. The device is to contain no batteries or accumulators where possible. Furthermore, the spraying device is to be operable independently of external energy sources, irrespective of location. The spraying device to be developed is to be suitable for manufacture substantially from inexpensive plastic injection-moulded parts. The device is to be able to drive a medical irrigation liquid and thus to produce a jet or spray cone formed from irrigation liquid droplets, wherein the irrigation liquid droplets are to be distributed randomly in the spray cone. Furthermore, the device is to function as quietly as possible.

The objects of the invention are achieved by a medical spraying device for irrigating a wound, in particular lavage system, comprising a liquid reservoir for a medical irrigation liquid or a connection for such a liquid reservoir and an arrangement for applying pressure to the medical irrigation liquid, such that the irrigation liquid can be pushed through a nozzle by the pressure acting on the irrigation liquid in order to produce a spray cone, wherein the nozzle has a plurality of openings, which are arranged at an angle to one another in such a way that the irrigation liquid jets exiting from the openings meet in an atomisation space and/or a discharge opening of the nozzle and thus produce the spray cone from the atomised irrigation liquid.

In this context, "immediately in front of the nozzle" means that the distance of the meeting point of the irrigation liquid jets is arranged closely in front of the nozzle in such a way that the pressure of the flow rate of the irrigation liquid is sufficient to atomise the irrigation liquid jets. In this respect, the maximum distance is dependent on the achievable flow rate of the irrigation liquid and therefore on the pressure acting on the irrigation liquid.

In accordance with the invention, the meeting point or the meeting points of the produced irrigation liquid jets may preferably lie within a distance of less than 2 mm, preferably of less than 1 mm in front of the openings of the nozzle.

A nebulisation of the irrigation liquid is thus achieved in the simplest manner without the need for a motor or a movable part in the nozzle for this purpose.

Here, the nozzle may have a central opening for producing a middle main jet and a plurality of outer openings arranged around the central opening, wherein preferably outer openings that are opposite one another with respect to the main opening are inclined at the same angle in the direction of the main jet.

A good nebulisation of the irrigation liquid is achieved with this embodiment, and a powerful spray jet is produced at the same time.

Further, at least two inlet openings may be arranged at the liquid inlet of the nozzle, such that the irrigation liquid entering the interior of the nozzle is divided into at least two irrigation liquid streams, which are conveyed in the nozzle to at least two openings in such a way that the at least two irrigation liquid jets meet at an angle of at least 10° in front of a discharge opening of the nozzle, and the irrigation liquid jets preferably meet at an angle between 10° and 85°, particularly preferably at an angle between 15° and 45°.

The nozzle thus performs all functions key for the production of the spray cone without thus complicating the construction. The nozzle can be manufactured easily from plastic.

With a development of the invention, it is also proposed for a gas to be contained above the irrigation liquid in the liquid reservoir, via which gas a pressure can be administered onto the irrigation liquid via the surface of the irrigation liquid.

In accordance with a development of the invention, the arrangement for applying pressure to the medical irrigation liquid may be a compressed gas reservoir, wherein the compressed gas reservoir is connected or connectable via a pressure line to the liquid reservoir, such that the irrigation liquid can be pushed through a nozzle by the gas pressure of the compressed gas reservoir acting on the irrigation liquid in order to produce the spray cone.

As a result of this construction, an external liquid reservoir can also be used.

Here, at least one pressure relief valve is arranged in the wall of the pressure line, which opens outwardly and closes the pressure line in accordance with the gas pressure from the compressed gas reservoir As a result of the use of the pressure relief valve the medical irrigation liquid can be acted on directly by the gas pressure from the pressure line and the spraying device can thus be constructed without a motor without resulting in dangerous overpressures in the spraying device. It can thus also be ensured that the spraying device can still be used safely, even in the case of a failure of the pressure reduction valve. The pressure relief valve preferably opens from a limit pressure between 2 bar and 6 bar.

With a preferred embodiment of the invention, it is proposed for the liquid reservoir to be delimited by a resilient wall, which deforms resiliently under the action of the gas pressure, such that the volume of the liquid reservoir reduces with a reduction of the gas pressure and in so doing the irrigation liquid is pushed out from the liquid reservoir through the nozzle.

Due to the resilience of the bottle or the walls, irrigation liquid can then also still be discharged if the gas pressure drops or fluctuates suddenly.

Furthermore, in accordance with the invention, the compressed gas reservoir may be a compressed gas cartridge, preferably a liquefied gas cartridge, particularly preferably a $CO_2$ cartridge, which is detachably connectable or connected to the pressure line, wherein the compressed gas cartridge is preferably connectable or connected to the pressure line via an opening means for the compressed gas cartridge.

The use of a compressed gas cartridge means that the spraying device is independent of an external compressed gas supply or power supply. Alternatively, the spraying device could also be equipped with a compressor and a power connection or an accumulator.

In embodiments with compressed gas cartridge, an evaporation space for the evaporation of liquid constituents of a liquefied gas from the compressed gas cartridge can be arranged in the pressure line between the connection for the compressed gas cartridge and the pressure relief valve, wherein the evaporating liquefied gas produces the gas pressure.

As a result, liquid constituents of the gas from the compressed gas cartridge or snow or other condensates created directly thereafter are thus prevented from penetrating deep into the pressure line and having an interfering effect there.

Further, a manually actuatable valve may be arranged in the pressure line at the connection for the compressed gas cartridge.

The spraying device can then be switched to a “ready” state.

Alternatively to a compressed gas cartridge, the compressed gas reservoir may be connected to a compressor, which is preferably connected via a flexible line to the spraying device.

The compressor may also be part of a large-area compressed gas network, which for example is available in a hospital.

With a preferred development, it is proposed for a pressure reduction valve to be arranged in the pressure line, said pressure reduction valve limiting the gas pressure that acts on the irrigation liquid in the liquid reservoir.

As a result of the use of the pressure reduction valve, it can be ensured that an excessive pressure is not produced in the following pressure line arranged thereafter and therefore in the liquid reservoir, which could potentially lead to a destruction of parts of the pressure line or of the walls of the liquid reservoir or of the bottle. In addition, a reasonably constant pressure thus presses on the irrigation liquid, and a uniform irrigation liquid flow can thus be applied through the nozzle.

Here, at least one safety element may be arranged between the pressure reduction valve and the liquid reservoir, in particular at least one bursting disc and/or at least one pressure relief valve, which limits the gas pressure loading the liquid reservoir.

In the case of irrigation devices according to the invention, the liquid reservoir can be connected or connectable via a liquid line to the nozzle, wherein a manually actuatable valve element is arranged in the liquid line, is preferably suitable for controlling the volume flow rate of the irrigation liquid, and is particularly preferably operable using a trigger.

The spray cone can thus be produced on account of manual operation.

Further, the liquid reservoir may be a bottle containing a medical irrigation liquid which is connected or connectable via the pressure line and/or via the liquid line to the spraying device, wherein the liquid line and the pressure line preferably discharge through the same opening in the bottle arranged head-down during operation.

The bottle is preferably connected or connectable via the pressure line and via the liquid line to the spraying device.

With this embodiment of the invention, a separate bottle containing the irrigation liquid can be used without having to fill the irrigation liquid into the device beforehand. The bottles can also be changed more easily if more than the content of one bottle is necessary for the treatment.

Furthermore, at least two inlet openings may preferably be arranged at the liquid inlet of the nozzle, such that the irrigation liquid entering the interior of the nozzle is divided into at least two irrigation liquid streams, which are conveyed in the nozzle to at least two openings in such a way that the at least two irrigation liquid jets meet at an angle of at least 10° in front of the discharge opening of the nozzle, and the irrigation liquid jets preferably meet at an angle between 10° and 85°, particularly preferably at an angle between 15° and 45°.

With a development of the invention, it is proposed for the nozzle to be provided as the tip of a discharge pipe, wherein the discharge pipe is preferably arranged so as to be displaceable relative to the spraying device telescopically in the axial direction of the discharge pipe and/or the discharge pipe is mounted so as to be rotatable axially through an angle of at least 30°.

The spraying device can thus be adapted well to different conditions and operation situations.

In accordance with the invention, the openings in the nozzle may also be arranged at an angle to one another in such a way that the irrigation liquid jets exiting from the openings meet in an atomisation space and/or a discharge opening of the nozzle.

The nebulisation or atomisation in the atomisation space prevents unatomised liquid droplets from detaching from the tip of the nozzle and from dripping in an uncontrolled manner. A more uniform spray cone is thus additionally achieved.

With a development of the invention, it is also proposed for a gas to be contained above the irrigation liquid in the liquid reservoir, via which gas a pressure can be administered onto the irrigation liquid over the surface of the irrigation liquid.

The objects of the invention are also achieved by the use of such a medical spraying device for producing a spray cone for debriding infected tissue.

Further, the objects of the invention are also achieved by a method for producing a spray cone of a medical irrigation liquid, in particular using such a spraying device, in which the irrigation liquid is pushed through a plurality of openings in a nozzle and the irrigation liquid jets thus produced are shot towards one another at such a flow rate and at such an angle that the irrigation liquid jets atomise in front of the nozzle and form a spray cone.

Here, a gas pressure is conveyed from a compressed gas reservoir through a pressure line into a liquid reservoir of the medical irrigation liquid, and the irrigation liquid is pushed out from the liquid reservoir through the nozzle by means of the gas pressure, wherein, if a limit pressure in the pressure line is exceeded, at least one pressure relief valve in the pressure line is opened and the compressed gas thus flows into the surrounding environment and the pressure in the pressure line is reduced, preferably limited Here, the gas pressure can again be produced by evaporating a gas from a liquid cartridge, in particular a $CO_2$ cartridge, wherein the gas is preferably liquefied in part in an evaporation space before it is conveyed to the pressure relief valve.

It is also proposed for the gas pressure to be limited using a pressure reduction valve in the pressure line, and for the gas pressure limited by the pressure reduction valve to be conveyed through the pressure line to the liquid reservoir of the medical irrigation liquid, wherein preferably the gas pressure between the pressure reduction valve and the liquid reservoir is reduced, preferably limited, in the case that the limit pressure is exceeded.

The invention is based on the surprising finding that it is possible with the aid of a nozzle having a plurality of openings of suitable arrangement to shoot towards one another the irrigation liquid jets from the nozzle, such that these jets are nebulised, and to produce a spray cone formed from a fine spray mist. The spraying device can thus be operated directly with gas pressure, such that a gas pressure acts directly on the medical irrigation liquid and thus is thus pressed through the nozzle, where the irrigation liquid is nebulised to form a spray cone. As a result of the direct use of the gas pressure as a drive for the irrigation liquid, the lavage system according to the invention does not require any motors or any rotating or oscillating parts to drive the irrigation liquid. The construction is thus simplified, and the lavage system can thus be manufactured as a disposable product to be used just once. In the medical field the manufacture as a single use product has the advantage that there is no need for disinfection of the lavage system, during which faults can occur and which can lead to a complicated infection in the patient with use of a contaminated lavage system. In addition, the entire construction can be formed very inexpensively.

The invention can thus be implemented in that at least two openings are arranged at the liquid inlet of the nozzle, such that the irrigation liquid entering the interior of the nozzle is divided into at least two irrigation liquid streams, which are conveyed in the interior of the nozzle such that they meet at an angle of at least 10° in front of the discharge opening of the nozzle. Due to the fact that the at least two irrigation liquid streams flow into one another or shoot towards one another, the irrigation liquid is atomised into the smallest liquid droplets, which move in a statistically distributed manner in the spray cone. There are thus no irrigation liquid jets, but randomly distributed individual droplets, such that the entire tissue area to be cleaned is contacted by individual irrigation liquid droplets with appropriate exposure of the spray cone. A cleaning effect of the spraying device is thus reliably ensured.

The directional indications "in front of" or "after" refer to the direction of flow of the compressed gas or of the medical irrigation liquid.

The medical spraying device preferably has at least one valve element, which regulates the irrigation liquid flow between the irrigation liquid container and the nozzle, wherein the nozzle is preferably arranged on a discharge pipe.

The valve element is particularly preferably connected to a trigger, which is to be actuated manually and which is held in the unactuated state by at least one spring, such that the irrigation liquid stream between the irrigation liquid container and the nozzle arranged on the discharge pipe is interrupted by the valve element.

Here, it is essential for the medical spraying device that the gas cartridge contains a non-toxic gas, or a non-toxic gas is used as gas for the gas reservoir. Examples of gases, in particular for gas cartridges, include argon, helium, nitrous oxide and carbon dioxide. It is particularly preferable if the gas cartridge contains liquid carbon dioxide, carbon dioxide being preferred as compressed gas. Carbon dioxide is inexpensive, non-toxic and has the key advantage that it can be stored without difficulty in liquefied form in compressed gas cartridges at room temperature. It is thus possible to provide large gas volumes in small-volume compressed gas cartridges.

The entire structure, except for the nozzle and, where applicable, the discharge pipe, is preferably arranged in accordance with the invention in a housing, wherein the housing is particularly preferably pistol-shaped, with the nozzle as the tip. The medical user can thus easily grasp and operate the spraying device.

A further advantageous embodiment of the invention lies in that the discharge pipe is arranged in the housing so as to be displaceable in the axial direction, wherein the discharge pipe is mounted so as to be rotatable about the longitudinal axis thereof through an angle of at least 30° and has at least one pin on the pipe end thereof opposite the nozzle. In an embodiment with discharge pipe, the pin may preferably grasp in accordance with the invention in a slotted guide in the housing, and at least two recesses are arranged perpendicularly to the slotted guide as a catch for the pin. This means that the length of the discharge pipe can be varied depending on the desired purpose by simply sliding the discharge pipe out from or into the housing. It is thus possible, without additional discharge pipes, to clean tissues areas in which a short discharge pipe is necessary, for example in the case of implantation of total knee joint endoprostheses, and it is also possible once the discharge pipe has been drawn out to clean tissue areas in which a long discharge pipe is necessary, for example in the case of implantation of hip stems. By rotating the discharge pipe about the longitudinal axis thereof, the pin of the discharge pipe can be locked in the desired position by latching into the recesses arranged perpendicularly to the guide in accordance with the principle of a bayonet closure.

Figure 2:
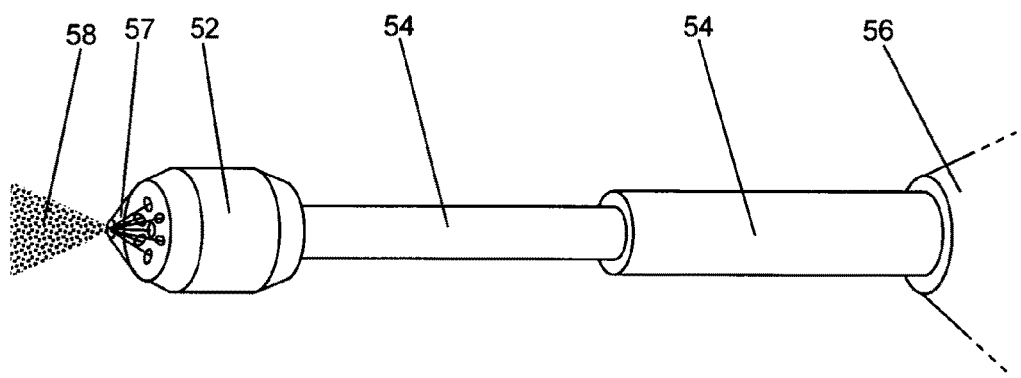

Exemplary embodiments of the invention will be explained hereinafter with reference to two schematically illustrated figures, without limiting the invention hereto. The figures showing:

FIG. 1: shows a schematic cross-sectional view through a medical spraying device according to the invention; and FIG. 2: shows a schematic perspective view of a nozzle and a telescopic discharge pipe of a medical spraying device according to the invention.

FIG. 1 shows a schematic cross-section through a medical spraying device according to the invention. A holder with an inner thread 1 for receiving an outer thread 2 of a $CO_2$ compressed gas cartridge 4 is provided on the rear face of the spraying device. A rotary handle piece 6 is fastened on the base of the compressed gas cartridge 4 in order to facilitate the rotation and fastening of the compressed gas cartridge 4 into the holder of the spraying device.

A hollow spike 8 is arranged in the holder and is used to open the compressed gas cartridge 4 and is connected to a pressure line 9 for the compressed gas. As the compressed gas cartridge 4 is rotated in, it pushes via a closure, provided for opening, onto the hollow spike 8, such that the compressed gas cartridge 4 opens and the compressed gas from the compressed gas cartridge 4 flows into the hollow spike 8 and therefore into the pressure line 9. An evaporation space 10 or an evaporation container 10 is arranged in the pressure line 9. Liquid constituents of the $CO_2$ gas or other snow-like condensates, which pass from the compressed gas cartridge into the pressure line 9, are collected there and can evaporate there gradually. As a result of this construction, liquid or snow-like constituents are prevented from penetrating deeper into the pressure line 9 and leading there to irregularities of the pressure as they evaporate.

Alternatively to the use of a compressed gas cartridge 4, a connection tube (not shown) of a compressed gas source, for example a compressor and/or a central compressed gas distribution arrangement (not shown), can also be connected to the pressure line 9. Under normal circumstances, the evaporation space 10 can then also be omitted.

A pressure reduction valve 12 is arranged in the further progression of the pressure line 9 and is illustrated here only as a circular disc for simplification. The pressure in the further pressure line 9 is limited by means of the pressure reduction valve 12 to a value between 1.5 bar and 8 bar. As is often the case with pressure reduction valves, the pressure set by the pressure reduction valve 12 can also be set with a pressure reduction valve 12 used here by means of an adjusting screw (not shown) and can be changed manually.

Two pressure relief valves 14, 15 are arranged in the further progression of the pressure line 9 after the pressure reduction valve 12 and open the pressure line 9 outwardly in the direction of the surrounding environment of the spraying device from a limit pressure between 2 and 10 bar. The pressure relief valves 14, 15 are constructed for example by balls mounted with steel springs in a cylindrical hollow space, wherein the balls are pushed by the steel springs on a ball surface in the direction of the pressure line 9 and thus seal off the pressure line 9. The cylindrical hollow space has at least one connection, outwardly to the surrounding environment of the spraying device, that cannot be covered by the balls. The pressure relief valves 14, 15 mean that no excessively high pressures can be created in the further pressure line 9, even if the pressure reduction valve 12 fails.

After the pressure relief valves 14, 15 formed as blockable T-pieces, the pressure line 9 continues as a flexible tube, which leads out for one or more meters from the spraying device, where it is then connected via a stopper or another connection means to a bottle 16 suspended head-down and made of a plastic. A medical irrigation liquid 18 for treating a wound, and a gas phase 20 arranged above the irrigation liquid are contained in the bottle 16.

The overpressure from the pressure line 9 discharges into the bottle 16 and expands the gas phase 20 arranged above and also the bottle 16, if this is resilient. Due to the gas pressure from the pressure line 9 and, where applicable, also due to the resilient pressure of the bottle 16, the medical irrigation liquid 18 is pressurised and is pushed through a liquid line 22 in the direction of a nozzle 24 of the irrigation device. The liquid line 22 is a flexible tube in the present case, which is introduced into the bottle 16 through the same stopper as the flexible tube of the pressure line 9. The stopper seals the bottle 16.

Most of the components of the medical spraying device are arranged in a housing 26 made of plastic, which is fixedly connected to the remaining parts and which has the form of a pistol with a pistol grip 28. The liquid line 22 and the flexible parts of the pressure line 9, which are arranged outside the housing 26, can be encased in a common flexible tube (not shown) in order to prevent the liquid line 22 and the external pressure line 9 from becoming entangled.

A manually operable valve element 30 spring-loaded by a steel spring is arranged inside the housing 26 between the nozzle 24 and the liquid line 22, and can be operated by means of a rotatably mounted trigger 32. In FIG. 1 the valve element 30 is shown in the closed position. The liquid line 22 is conveyed after the valve element 30 through a discharge pipe 34 to the nozzle 24. The discharge pipe 34 can preferably be extended telescopically (not shown). Further, the nozzle 24 can be inclined with respect to the axis of the discharge pipe 34 and rotatably mounted.

When the valve element 30 is operated via the trigger 32, a continuous line of the irrigation liquid 18 is formed from the bottle 16 to the nozzle 24. A number of channels 36 are provided in the nozzle 24, such that the liquid stream of the irrigation liquid 18 is divided within the nozzle 24 into a number of liquid streams. The channels 36 are guided such that the irrigation liquid jets (not shown) flowing out after the nozzle 24 meet one another or are shot towards one another at an angle between 10° and 80° in an atomisation space 38 or in a discharge opening of the nozzle 24. The outer irrigation liquid jets can run here along the inner wall of the atomisation space 38 and meet the central main jet in the region of the central discharge opening (to the left in FIG. 1) of the nozzle 24. The meeting irrigation liquid jets atomise or nebulise here due to their kinetic energy in the atomisation space 38 to form a spray cone of fine irrigation liquid droplets (not shown), which exits through the front discharge opening.

A spray cone of a medical irrigation liquid can thus be produced with the device in the simplest manner, without the need for a motor or other constantly moving parts for this purpose. The construction can be constructed substantially from plastic parts, which can be produced by simple injection moulding processes.

FIG. 2 shows a schematic perspective view of a nozzle 52 and a telescopic discharge pipe 54 of a medical spraying device according to the invention. The discharge pipe 54 protrudes from a housing 56 of the spraying device. The rest of the spraying device corresponds for example to the construction according to FIG. 1. The nozzle 52 is rotationally symmetrical externally.

Inside the nozzle 52, a liquid stream of a medical irrigation liquid flowing through the discharge pipe 54 is divided into six partial streams, which discharge through six openings on the front face of the nozzle 52, as can be seen in FIG. 2. The front face of the nozzle 52 is curved in the direction of the centre of the nozzle 52. A conical cap made of a transparent plastic is arranged in front of this front face. The plastic does not have to be transparent, but in the present case this facilitates the description of the nozzle function with FIG. 2. An atomisation space 57 is formed between the conical cap and the front face of the nozzle 52. The atomisation space 57 has a central discharge opening, in which liquid jets from the openings meet.

The seven liquid lines inside the nozzle 52, apart from the liquid line for the middle main jet, are inclined in the region of the openings in the direction of the axis of symmetry of the external form of the nozzle 52. The inclinations of the lines all have the same angle with respect to the axis of symmetry of the external form of the nozzle 52 or with respect to the central main jet, and the six openings are distributed symmetrically about this axis of symmetry or the main jet at equal distances therefrom on the front face of the nozzle 52.

Seven irrigation liquid jets (indicated by lines in FIG. 2), which come from the openings, thus all meet in a region (the discharge opening), atomise or nebulise in the atomisation space 57, and form a spray cone 58 of the medical liquid in front of the nozzle 52 when an irrigation liquid is pushed from the rear face of the nozzle 52 by the spraying device into the nozzle 52.

The telescopic construction of the discharge pipe 54 is used to make the spraying device universally usable in different locations of use. To this end, the inclination of the nozzle 52 with respect to the discharge pipe 54 can preferably be adjusted in accordance with the invention.

The features of the invention disclosed in the above description and in the claims, figures and exemplary embodiments can be essential both individually and in any arbitrary combination for the implementation of the invention in the various embodiments thereof.

LIST OF REFERENCE SIGNS

1 inner thread
2 outer thread
4 compressed gas reservoir/compressed gas cartridge
6 rotary handle piece
8 hollow spike
9 pressure line
10 evaporation space
12 pressure reduction valve
14 pressure relief valve
15 pressure relief valve
16 bottle
18 medical irrigation liquid
20 gas phase arranged above
22 liquid line
24 nozzle
26 housing
28 pistol grip
30 valve element
32 trigger
34 discharge pipe
36 channel
38 atomisation space
52 nozzle
54 discharge pipe
56 housing
57 atomisation space
58 spray cone

The invention claimed is:

1. A medical spraying device for irrigating a wound comprising a liquid reservoir for a medical irrigation liquid or a connection for such a liquid reservoir and an arrangement for applying pressure to the medical irrigation liquid, such that the irrigation liquid is pushable through a nozzle by the pressure acting on the irrigation liquid to produce a spray cone, wherein the nozzle has a plurality of openings, that are arranged at an angle to one another such that irrigation liquid jets exiting from the openings meet in an atomization space or in a discharge opening of the nozzle adjacent to the atomization space and produce the spray cone from the atomized irrigation liquid, wherein the atomization space is formed between a front face of the nozzle and the discharge opening of the nozzle and gradually decreases in diameter in a direction towards the discharge opening of the nozzle, and further wherein the resulting spray cone outwardly increases in diameter starting from the discharge opening of the nozzle.

2. The spraying device according to claim 1, wherein the nozzle has a central opening for producing a middle main jet and a plurality of outer openings arranged around the central opening, wherein the outer openings, that are opposite one another with respect to the main opening, are inclined at the same angle in the direction of the main jet.

3. The spraying device according to claim 1, wherein the arrangement for applying pressure to the medical irrigation liquid is a compressed gas reservoir, wherein the compressed gas reservoir is connected via a pressure line to the liquid reservoir, such that the irrigation liquid is pushable by the gas pressure of the compressed gas reservoir acting on the irrigation liquid through the nozzle to produce the spray cone.

4. The spraying device according to claim 3, wherein at least one pressure relief valve is arranged in a wall of the pressure line, that opens outwardly and closes the pressure line via the gas pressure from the compressed gas reservoir.

5. The spraying device according to claim 3, wherein the liquid reservoir is delimited by a resilient wall, that deforms resiliently under the action of the gas pressure, such that, with a reduction of the gas pressure, a volume of the liquid reservoir reduces and pushes the irrigation liquid out from the liquid reservoir through the nozzle.

6. The spraying device according to one of claim 3, wherein the compressed gas reservoir is a liquefied gas cartridge, that is detachably connectable to the pressure line, wherein the compressed gas cartridge is connectable to the pressure line via an opening means for the compressed gas cartridge.

7. The spraying device according to claim 6, wherein the evaporation space for the evaporation of liquid constituents of a liquefied gas from the liquefied gas cartridge is arranged in the pressure line between the connection for the compressed gas cartridge and the pressure relief valve, wherein the evaporating liquefied gas produces the gas pressure.

8. The spraying device according to claim 6, wherein a manually actuatable valve is arranged in the pressure line at the connection for the liquefied gas cartridge.

9. The spraying device according to claim 1, wherein the compressed gas reservoir is connected to a compressor, that is connectable via a flexible line to the spraying device.

10. The spraying device according to claim 3, wherein a pressure reduction valve is arranged in the pressure line, that limits the gas pressure acting in the liquid reservoir on the irrigation liquid.

11. The spraying device according to claim 10, wherein at least one safety element is arranged between the pressure reduction valve and the liquid reservoir and limits the gas pressure loading the liquid reservoir.

12. The spraying device according to claim 1, wherein the liquid reservoir is connected or connectable via a liquid line to the nozzle, wherein a manually actuatable valve element is arranged in the liquid line, is adapted for controlling a volume flow rate of the irrigation liquid, and is operable using a trigger.

13. The spraying device according to claim 3, wherein the liquid reservoir is a bottle containing a medical irrigation liquid that is connectable via the pressure line or the liquid line to the spraying device, wherein the liquid line and the pressure line are configured to discharge through a same opening in the bottle arranged head-down during operation.

14. The spraying device according to claim 1, wherein at least two inlet openings are arranged at the liquid inlet of the nozzle, such that the irrigation liquid entering the interior of the nozzle is divided into at least two irrigation liquid streams, that are conveyed in the nozzle to at least two openings such that the at least two irrigation liquid streams meet at an angle of at least 10° in front of a discharge opening of the nozzle.

15. The spraying device according to claim 1, wherein the nozzle is provided as a tip of a discharge pipe, wherein the discharge pipe is arranged to be displaceable relative to the spraying device telescopically in an axial direction of the discharge pipe or the discharge pipe is mounted to be rotatable axially through an angle of at least 30°.

16. The spraying device according to claim 1, wherein a gas is contained above the irrigation liquid in the liquid reservoir, wherein a pressure, via the gas, can be administered onto the irrigation liquid via the surface of the irrigation liquid.

17. A method for debriding infected tissue comprising: producing a spray cone, for debriding infected tissue, via the spraying device according to claim 1.

18. A method for producing at least one spray cone of a medical irrigation liquid using the spraying device according to claim 1, the method comprising:
pushing irrigation liquid through the plurality of openings in the nozzle, of the spraying device according to claim 1, such that the irrigation liquid jets are produced shot towards one another at a flow rate and at an angle that the irrigation liquid jets atomise in front of the nozzle and form a spray cone.

19. The method according to claim 18, wherein a gas pressure is conveyed from a compressed gas reservoir through a pressure line into a liquid reservoir of the medical irrigation liquid, and the irrigation liquid is pushed out from the liquid reservoir through the nozzle by means of the gas pressure, wherein, if a limit pressure in the pressure line is exceeded, at least one pressure relief valve in the pressure line is opened and the compressed gas thus flows into the surrounding environment and the pressure in the pressure line is reduced or limited.

20. The method according to claim 19, wherein the gas pressure is produced by evaporating a gas from a $CO_2$ cartridge, wherein the gas is liquefied, at least in part, in an evaporation space before it is conveyed to the pressure relief valve (14, 15).

21. The method according to claim 19, wherein the gas pressure is limited using a pressure reduction valve in the pressure line, and the gas pressure limited by the pressure reduction valve is conveyed through the pressure line to the liquid reservoir of the medical irrigation liquid, wherein the gas pressure between the pressure reduction valve and the liquid reservoir is reduced or limited, if a limit pressure is exceeded.

22. The spraying device according to claim 1, wherein at least two inlet openings are arranged at the liquid inlet of the nozzle, such that the irrigation liquid entering the interior of the nozzle is divided into at least two irrigation liquid streams, that are conveyed in the nozzle to at least two openings such that the at least two irrigation liquid jets meet at an angle between 15° and 45° in front of a discharge opening of the nozzle.

* * * * *